United States Patent [19]

Kassebaum et al.

[11] Patent Number: 5,430,005
[45] Date of Patent: Jul. 4, 1995

[54] HERBICIDAL COMPOSITIONS

[75] Inventors: James W. Kassebaum, Manchester, Mo.; Shuaib A. Khan, Auderghem, Belgium

[73] Assignee: Monsanto Company, St. Louis, Mo.

[21] Appl. No.: 739,554

[22] Filed: Aug. 2, 1991

[51] Int. Cl.$^6$ .................. A01N 25/30; A01N 57/04
[52] U.S. Cl. .................. 504/206; 71/DIG. 1
[58] Field of Search .............. 71/86, DIG. 1; 504/206

[56] References Cited

U.S. PATENT DOCUMENTS

| | | | |
|---|---|---|---|
| 3,123,640 | 3/1964 | Longley | 260/567.6 |
| 3,123,641 | 3/1964 | Longley | 260/567.6 |
| 4,159,901 | 7/1979 | Beestman et al. | 71/86 |
| 4,399,287 | 8/1983 | Baillie et al. | 71/86 |
| 4,414,158 | 11/1983 | Thummel et al. | 71/86 |
| 4,439,428 | 3/1984 | Cox | 424/200 |
| 5,118,444 | 6/1992 | Nguyen | 252/390 |

FOREIGN PATENT DOCUMENTS

| | | |
|---|---|---|
| 0357553 | 3/1990 | European Pat. Off. |
| 2589328 | 10/1986 | France |
| 2230955 | 11/1990 | United Kingdom |

OTHER PUBLICATIONS

J. B. Wyrill et al. *Weed Science*, vol. 25, Issue 3 (May) 1977, pp. 275–287.

*Primary Examiner*—S. Mark Clardy
*Attorney, Agent, or Firm*—Stanley M. Tarter; Gordon F. Sieckmaun; Richard H. Shear

[57] ABSTRACT

A herbicidal composition is provided which comprises: an aqueous solution of a herbicidally acceptable salt of N-phosphonomethylglycine; a quaternary ammonium compound represented by the formula

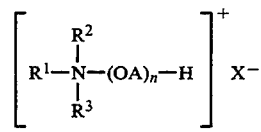

wherein each A represents an alkylene group having 2 or 3 carbon atoms, $R^1$ and $R^2$ are each independently an alkyl or alkanol group having from 1 to 3 carbon atoms; $R^3$ is an alkyl group having from 1 to 3 carbon atoms or a group having the formula $(AO)_m$—H; n (in a compound in which $R^3$ is an alkyl group) or n+m (in a compound in which $R^3$ is a group having the formula $(AO)_m$—H), has a value of from 2 to 15; and $X^-$ is a halide or phosphate; and a glycol selected from the group consisting of propylene glycol, and polypropylene glycol having an average molecular weight up to about 1000; wherein the weight ratio of N-phosphonomethylglycine to the quaternary ammonium compound is between about 1:5 to about 5:1; and the weight ratio of glycol to the quaternary ammonium compound is between about 1:40 and about 1:2 at a pH between pH 4 and pH 7 to provide a clear solution.

10 Claims, No Drawings

HERBICIDAL COMPOSITIONS

BACKGROUND OF THE INVENTION

This invention relates to herbicidal compositions, and wore particularly relates to herbicidal compositions containing N-phosphonomethylglycine, a quaternary ammonium compound and propylene glycol or polypropylene glycol.

N-Phosphonomethylglycine, known in the agricultural chemical art as glyphosate, is a highly effective and commercially important phytotoxicant useful in controlling the growth of germinating seeds, emerging seedlings, maturing and established woody and herbaceous vegetation, and aquatic plants. N-phosphonomethylglycine and its salts are conveniently applied in an aqueous formulation as a post-emergent phytotoxicant for the control of numerous plant species. N-Phosphonomethylglycine and its salts are characterized by a broad spectrum activity, i.e., they control growth of a wide variety of plants.

Commercial compositions containing N-phosphonomethylglycine are usually aqueous solutions wherein the N-phosphonomethylglycine is present as a herbicidally acceptable salt, such as the trimethyl sulfonium salt, an alkali metal salt, the ammonium salt or the salt of an amine having a molecular weight of less than about 300. The monoisopropylamine salt of N-phosphonomethylglycine is the most widely used salt in such aqueous compositions. In addition, such compositions usually contain a surfactant to enhance the effectiveness of the N-phosphonomethylglycine when it is applied to the foliage of various plants. The most widely used surfactant in commercial compositions is an ethoxylated fatty acid amine.

It is known to those skilled in the art that a particular surfactant used in an aqueous composition with a herbicide can enhance the effectiveness of the herbicide, whereas other surfactants have very little, if any beneficial effect, and in fact, some may be antagonistic. Wyrill and Burnside, *Weed Science*, Vol. 25 (1977), p 275-287, examined solutions containing different classes of surfactants, including polyoxyethylene stearyl methyl ammonium chlorides containing respectively 2 and 15 oxyethylene units. Some classes of surfactant were more effective than others in enhancing the herbicidal effect of N-phosphonomethylglycine (used as a solution of the isopropylamine salt), and Wyrill and Burnside concluded that an effective surfactant is a critical component of any aqueous composition containing N-phosphonomethylglycine.

Although certain surfactants may enhance the biological activity of N-phosphonomethylglycine, many of such surfactants are difficult to incorporate into aqueous compositions containing N-phosphonomethylglycine because of the pH and the ionic strength of the aqueous composition, and other factors that effect viscosity, haziness and other physical characteristics that are desired by the end user. In addition, even though N-phosphonomethylglycine is known to be relatively non-toxic and environmentally acceptable, the surfactant in some situations can be toxic to aquatic life, and/or cause skin irritation or eye irritation when in contact with the skin or the eye.

Accordingly, it would be desirable to obtain an aqueous composition containing N-phosphonomethylglycine which employs a surfactant that enhances the biological effect of N-phosphonomethylglycine but would have lower irritation and toxicity than other surfactants. It has been found that certain quaternary ammonium compounds disclosed in U.S. Pat. No. 3,619,351 are effective in enhancing the herbicidal activity of N-phosphonomethylglycine, and that aqueous compositions containing such quaternary ammonium compounds are virtually non-toxic and non-irritating to the skin and eye. However, such aqueous compositions containing the quaternary ammonium compounds are often hazy, indicating that the surfactant is only partially in solution, and will result in phase separation over time and require agitation before use. The phase separation will decrease the biological effectiveness of the formulation, as well as being aesthetically undesirable to the end user.

Now it has been found that an aqueous composition can be prepared which incorporates all the desired properties of enhancing the biological activity of N-phosphonomethylglycine, is virtually non-toxic and non-irritating to the skin and eye, and which is not hazy, but rather is a clear solution.

SUMMARY OF THE INVENTION

These and other advantages are achieved in a herbicidal composition which comprises: an aqueous solution of a herbicidally acceptable salt of N-phosphonomethylglycine; a quaternary ammonium compound represented by the formula

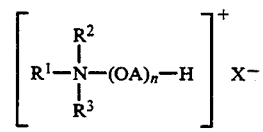

wherein each A represents an alkylene group having 2 or 3 carbon atoms, $R^1$ and $R^2$ are each independently an alkyl or alkanol group having from 1 to 3 carbon atoms; $R^3$ is an alkyl group having from 1 to 3 carbon atoms or a group having the formula $(AO)_m$—H; n (in a compound in which $R^3$ is an alkyl group) or n+m (in a compound in which $R^3$ is a group having the formula $(AO)_m$—H) has a value of from 2 to 15; and $X^-$ is a halide or phosphate; and a glycol selected from the group consisting of propylene glycol, and polypropylene glycol having an average molecular weight up to about 1000; wherein the weight ratio of N-phosphonomethylglycine to the quaternary ammonium compound is between about 1:5 to about 5:1; the weight ratio of glycol to the quaternary ammonium compound is between about 1:40 to about 1:2; and the pH is between about pH 4 and pH 7 to provide a clear solution.

DETAILED DESCRIPTION OF THE INVENTION

As noted above, N-phosphonomethylglycine is a well-known herbicide, and numerous methods are known in the art for preparing this compound. It is also known in the art that N-phosphonomethylglycine is relatively insoluble in water, and that to prepare aqueous compositions containing N-phosphonomethylglycine, it is desirable to prepare a herbicidally effective salt of N-phosphonomethylglycine. Such herbicidally effective salts include the trimethyl sulfonium salt, the alkali metals, ammonium or the salt of an organic amine. To obtain the salt it is only necessary to react the acid, N-phosphonomethylglycine, with aqueous solutions of the alkali metal hydroxides, such as lithium hydroxide, sodium hydroxide, potassium hydroxide, and the like; alkali metal carbonates, such as sodium carbonate, potassium carbonate and the like; or ammonium hydroxide or ammonium carbonate. Organic amines that have a molecular weight below about 300 can also be used. Such organic amines include the alkyl amines, alkylene amines and alkanol amines containing not more than 2 amine groups, such as methylamine, ethylamine, n-propylamine, isopropylamine, n-butylamine, isobutylamine, sec-butylamine, n-amylamine, iso-amylamine, hexylamine, heptylamine, octylamine, nonylamine, decylamine, undecylamine, dodecylamine, tridecylamine, tetradecylamine, pentadecylamine, hexadecylamine, heptadecylamine, octadeclyamine, methylethylamine, methylisopropylamine, methylhexylamine, methylnonylamine, methylpentadechylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, diheptylamine, dioactylamine, trimethylamine, triethylamine, tri-n-propylamine, triisopropylamine, tri-n-butylamine, triisobutylamine, tri-sec-butylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentenyl-2-amine, 2,3-dimethylbutenyl-2-amine, di-butenyl-2-amine, n-hexenyl-2-amine and propylenediamine, primary aryl amines such as aniline, methoxyaniline, ethoxyaniline, o,m,p-toluidine, phenylenediamine, 2,4, 6-tribromoaniline, benzidine, naphthylamine, o,m,p-chloroaniline, and the like; hetrocyclic amines such as pyridine, morpholine; piperidine, pyrrolidine, indoline, azepine and the like. Isopropylamine is preferred.

The quaternary ammonium compounds of the present composition are also those known to the art. Preferred compounds are those wherein $R^1$, $R^2$ and $R^3$ are each independently selected from methyl, ethyl and ethanol groups, and $X^-$ is chloride or phosphate. Even more preferred are compounds wherein $R^1$, $R^2$ and $R^3$ are each independently selected from methyl and ethyl groups, $X^-$ is chloride or phosphate and —$(AO)_n$— is -ethylene oxide(propylene oxide)$_n$— wherein n is between 6 and 10. Examples of the most preferred compounds wherein n averages about 8, include trimethylethoxypolypropoxyammonium chloride, methyldiethylethoxypropoxyammonium chloride, diethylethoxypolypropoxy ethanol ammonium phosphate, and the like. As will occur to those skilled in the art, in any particular instance several different compounds wherein n can vary over a narrow range will normally be present so that the values of n are to be understood as average values.

In the compositions of the present invention the weight ratio of N-phosphonomethylglycine (expressed as its acid equivalent) to the quaternary ammonium compound can vary over a wide range, for example, from about 1:5 to about 5:1. The optimum ratio will vary according to the manner in which the herbicidal composition is applied, the weed species to be treated, and the particular quaternary ammonium compound selected, but is normally between about 1:2 to about 4:1, for example, 2:1.

Commercial preparations of the preferred quaternary ammonium compounds of the present invention can contain polypropylene glycols as impurities. The quantity of this impurity is likely related to the amount of water present in the starting materials, and has been observed to be as low as 3% or as high as 33% of the commercial preparations. In most cases, the average degree of polymerization of the polypropylene glycol will be 2n, where n is as described above.

Although aqueous formulations containing a herbicidally acceptable salt of N-phosphonomethylglycine and the quaternary ammonium compound provide satisfactory results with respect to biological efficacy, toxicology and irritation, it has now been found that the presence of propylene glycol and/or polypropylene glycol having an average molecular weight of up to about 1000 in the composition improves the biological effectiveness of the composition, and the greatest biological effectiveness is observed in compositions containing polypropylene glycol having an average molecular weight greater than about 600. Although the composition can contain a polypropylene glycol having an average molecular weight in excess of about 1000, the solubility of such higher molecular weight polypropylene glycols in an aqueous composition decreases.

When polypropylene glycol having a molecular weight of above about 600 is used, it is necessary to increase the pH of the aqueous composition from its natural pH to provide a clear composition. The pH of the composition can readily be increased by the addition of base, which has an affect on the ionic characteristics of N-phosphonomethylglycine, and increases the ionic strength of the solution. Alternatively, water-soluble salts, such as tetramethyl ammonium chloride, can be added to provide a clear composition at its natural pH. Other salts, including inorganic as well as organic salts, may also be used. Also, alternatively, propylene glycol may be added to provide a clear composition at its natural pH, although more propylene glycol is required, on a weight basis, than base or added salt to provide a clear composition. Accordingly, it is preferred to use a polypropylene glycol having an average molecular weight between about 300 and 500 to provide a clear formulation without the addition of base, salt, or propylene glycol. It is even more preferred to use a polypropylene glycol that has a molecular weight of above about 600 with the addition of base, salt, or propylene glycol to provide a clear composition that has more improved biological effectiveness.

The pH effect to provide a clear composition is indeed surprising since with all other surfactants that Applicants have observed, raising the pH makes the surfactant less compatible in a herbicidal composition containing N-phosphonomethylglycine. The natural pH of an aqueous solution of the monoisopropylamine salt of N-phosphonomethylglycine is about pH 4.7. When the composition contains a polypropylene glycol having an average molecular weight greater than about 600, the pH can be increased to as high as pH 7 to provide a clear composition, but a clear composition is usually obtained at a pH below about pH 6. The effect of added salt to provide a clear composition is also surprising, since added salt usually decreases the solubility of surfactants in aqueous solution.

The weight ratio of polypropylene glycol to the quaternary ammonium compound can vary within wide limits. At a weight ratio of polypropylene glycol to the quaternary ammonium compound of less than about 1:40, the positive effects of the presence of the polypropylene glycol to the formulation to enhance the biological effectiveness and maintain a clear composition of the present invention may not be observed. At a weight ratio of polypropylene glycol to quaternary ammonium compound of greater than about 1:2, phase separation can occur in the formulation and a clear, one phase composition may not be possible. A preferred weight ratio of polypropylene glycol to the quaternary ammonium compound between about 1:40 and about 1:2 can readily be determined by those skilled in the art, depending upon the particular quaternary ammonium compound used in the composition and the average molecular weight of the polypropylene glycol.

The compositions of the present invention can be a liquid concentrate containing up to 400 grams per liter of N-phosphonomethylglycine or the composition can be diluted with water to form a spray containing about 1% N-phosphonomethylglycine for application to foliage of plants. A 0.1 to 2% concentration of N-phosphonomethylglycine in a spray provides complete herbicidal activity for most plants. The concentration of the N-phosphonomethylglycine in the present composition for application to plants is within the skill of the art. The present compositions can also contain other additives and active ingredients, such as ammonium sulfate or 2,4-dichlorophenoxyacetic acid. The invention is further illustrated by, but not limited to, the following examples wherein all parts are by weight unless otherwise indicated.

EXAMPLES 1-14

A series of compositions were prepared containing various quaternary ammonium compounds and polypropylene glycol. The results are summarized in Table I. In Table I the quaternary ammonium compound identified as "A" is a quaternary ammonium compound which is trimethyl ethoxy polypropylene (8 PO) ammonium chloride; quaternary ammonium compound "B" is methyldiethylethoxypolypropoxy (8 PO) ammonium chloride; and quaternary ammonium compound "C" is diethylethoxypolypropoxy (8 PO) ethanol ammonium phosphate. Each of the quaternary ammonium compounds contained polypropylene glycol having an average molecular weight between 600 and 1000 as an impurity, in the amount of 15%, 3% and 8%, respectively. The active quaternary ammonium compound in each of the commercial preparations was 85%, 97%, and 89.5%, respectively. Compound C also had 2.5% ethylene glycol as an impurity. Thus, each of the compositions had 13.18% active quaternary ammonium compound. Additional polypropylene glycol was added to the compositions as indicated in the Table 1. The pH is increased in Examples 2-6, 8, 9, 11 and 12 by adding additional isopropylamine to increase the pH to the indicated levels. All compositions contain N-phosphonomethylglycine equivalent to about 485 g/l as the monoisopropylamine salt.

TABLE I

| Example | Quat. Amm. Cmpd. (Identity) | Quat. Amm. Cmpd. (Weight %) | PPG as Impurity (Weight %) | Added PPG (MW) | Added PPG (Weight %) | Total PPG (Weight %) | pH | Appearance |
|---|---|---|---|---|---|---|---|---|
| 1 | A | 15.50 | 2.32 | — | — | 2.32 | 4.7 | hazy |
| 2 | A | 15.50 | 2.32 | — | — | 2.32 | 5.4 | clear |
| 3 | A | 15.50 | 2.32 | — | — | 2.32 | 5.9 | clear |
| 4 | B | 13.58 | 0.40 | — | — | 0.40 | 4.7 | clear |
| 5 | B | 13.58 | 0.40 | — | — | 0.40 | 5.4 | clear |
| 6 | B | 13.58 | 0.40 | — | — | 0.40 | 5.9 | clear |
| 7 | B | 13.58 | 0.40 | 425 | 1.92 | 2.32 | 4.7 | clear |
| 8 | B | 13.58 | 0.40 | 425 | 1.92 | 2.32 | 5.4 | clear |
| 9 | B | 13.58 | 0.40 | 425 | 1.92 | 2.32 | 5.9 | clear |
| 10 | B | 13.58 | 0.40 | 1000 | 1.92 | 2.32 | 4.7 | hazy |
| 11 | B | 13.58 | 0.40 | 1000 | 1.92 | 2.32 | 5.4 | hazy |
| 12 | B | 13.58 | 0.40 | 1000 | 1.92 | 2.32 | 5.9 | clear |
| 13 | C | 14.72 | 1.18 | — | — | 1.18 | 4.7 | hazy |
| 14 | C | 14.72 | 1.18 | — | — | 1.18 | 5.9 | clear |

From the data it can be seen that Examples 4, 5 and 6, containing low amounts of polypropylene glycol, produced clear compositions at each pH. Examples 7, 8 and 9 containing higher amounts of polypropylene glycol also produced clear compositions at each pH, but most of the polypropylene glycol had an average molecular weight below about 600. Examples 1, 2 and 3, which contained polypropylene glycol with an average molecular weight between about 600 and 1000, were hazy at pH 4.7 but were clear at higher pH levels. Examples 13 and 14 also showed this trend. Examples 10, 11 and 12, which contained polypropylene glycol with an average molecular weight between 600 and 1000, were not clear at pH 4.7 or pH 5.4, but were clear at pH 5.9. Thus, when the pH was adjusted upward in compositions containing higher amounts of polypropylene glycol with an average molecular weight between 600 and 1000, a clear composition was obtained.

EXAMPLES 15-19

Example 1 was modified to include tetramethyl ammonium chloride (TMAC) or tetraethyl ammonium chloride (TEAC). The results are summarized in Table 2. The compositions were all at the natural pH of 4.7.

From the data, it can be seen, comparing Example 1 to Example 15 where the pH is the same, that the addition of 2.5% TMAC produced a clear composition without any increase in pH. TMAC at 5% had the same effect. With 1.25% TEAC, Example 17 was still hazy, but further addition to 2.5% TEAC provided a clear composition at pH 4.7.

TABLE 2

| Example | Ammonium Chloride Salt Identity | Ammonium Chloride Salt (Wt. %) | Appearance |
|---|---|---|---|
| 15 | TMAC | 2.50 | clear |
| 16 | TMAC | 5.00 | clear |
| 17 | TEAC | 1.25 | hazy |
| 18 | TEAC | 2.50 | clear |
| 19 | TEAC | 5.00 | clear |

EXAMPLES 20-23

Example 1 was modified by the addition of propylene glycol. The results are summarized in Table 3. The compositions were all at the natural pH of 4.7.

From the data, it can be seen, comparing Example 1 to Examples 20-23, where the pH is the same, the addition of 2.5% to 7.5% propylene glycol still produced a hazy composition. However, when 10.0% propylene glycol was added, a clear composition at pH 4.7 was provided.

TABLE 3

| Example | Propylene glycol (Weight %) | Appearance |
| --- | --- | --- |
| 20 | 2.50 | hazy |
| 21 | 5.00 | hazy |
| 22 | 7.50 | hazy |
| 23 | 10.00 | clear |

EXAMPLE 24

The compositions of Examples 1-12 are used in investigating their effect on the biological action of glyphosate as compared to the commercial formulation containing glyphosate plus a tallow amine surfactant. In such tests downy brome (Brome) and Indian mustard (Mustard) plants are grown in a greenhouse from seed in 10 cm pots containing a natural loam soil enriched with a mixture of fertilizer. Irrigation is supplied by surface or from below to maintain soil moisture throughout the duration of the tests. The environment is controlled at a temperature regiment of 18° C. (day) and 12° C. (night). The relative humidity of 65% (day) and 75% (night) is used.

Before spraying and after two weeks, the pots are selected for uniformity as far as possible, and atypical samples are discarded. Spray solutions are supplied with a sprayer, calibrated to deliver spray solutions in one pass at a rate equivalent to 52 l/ha (20 gal./acre) of a 360 g/l glyphosate solution. After treatment control plots are placed at random among treated pots. Assessment of "percent final toxicity" are made 23 days after treatment by comparison with untreated controls and with controls sprayed with a glyphosate solution containing an ethoxylated tallow amine surfactant in a weight ratio of 2:1 N-phosphonomethylglycine to surfactant. The pots are evaluated on an arbitrary scale from 0 to 100% where 0 means no visible effect and 100% means complete death. For any one assessment all pots are rated by the same individual, assessments being performed "blind" (without knowledge of the treatment). The results reported in Table 4 indicate that the composition of the present invention containing polypropylene glycol with a molecular weight of greater than 600 are equivalent to the phytotoxic effect achieved with commercial N-phosphonomethylglycine plus an ethoxylated tallow amine used as the standard. Compositions containing polypropylene glycol with an average molecular weight of less than 600 are slightly less effective than the commercial standard, and formulations that fall outside the scope of the present invention provide the poorest results. Each value reported is the average of three readings.

TABLE 4

| Formulation | Rate (g/ha) | % Inhibition Brome | % Inhibition Mustard |
| --- | --- | --- | --- |
| 1 | 45.95 | 13.3 | 3.3 |
|   | 91.90 | 51.7 | 43.3 |
|   | 137.85 | 71.7 | 66.7 |
| 2 | 45.95 | 23.3 | 8.3 |
|   | 91.90 | 63.3 | 41.7 |
|   | 137.85 | 75.0 | 66.7 |
| 3 | 45.95 | 15.0 | 3.3 |
|   | 91.90 | 53.3 | 38.3 |
|   | 137.85 | 78.3 | 73.3 |
| 4 | 45.95 | 8.3 | 5.0 |
|   | 91.90 | 45.0 | 46.7 |
|   | 137.85 | 76.7 | 63.3 |
| 5 | 45.95 | 5.0 | 11.7 |
|   | 91.90 | 53.3 | 45.0 |
|   | 137.85 | 68.3 | 70.0 |
| 6 | 45.95 | 5.0 | 6.7 |
|   | 91.90 | 33.3 | 36.7 |
|   | 137.85 | 75.0 | 70.0 |
| 7 | 45.95 | 16.7 | 10.0 |
|   | 91.90 | 45.0 | 40.0 |
|   | 137.85 | 75.0 | 66.7 |
| 8 | 45.95 | 21.7 | 6.7 |
|   | 91.90 | 53.3 | 38.3 |
|   | 137.85 | 75.0 | 61.7 |
| 9 | 45.95 | 25.0 | 8.3 |
|   | 91.90 | 40.0 | 35.0 |
|   | 137.85 | 80.0 | 71.7 |
| 10 | 45.95 | 18.3 | 6.7 |
|   | 91.90 | 48.3 | 45.0 |
|   | 137.85 | 80.0 | 73.3 |
| 11 | 45.95 | 23.3 | 0.0 |
|   | 91.90 | 51.7 | 48.3 |
|   | 137.85 | 78.3 | 73.3 |
| 12 | 45.95 | 36.7 | 13.3 |
|   | 91.90 | 63.3 | 48.3 |
|   | 137.85 | 78.3 | 73.3 |
| Standard | 45.95 | 26.7 | 15.0 |
|   | 91.90 | 60.0 | 65.0 |
|   | 137.90 | 80.0 | 85.0 |
| Control | 0 | 0.0 | 0.0 |

EXAMPLE 25

Standard skin and eye irritation tests are carried out using the compositions of Examples 1-12 on New Zealand white rabbits by the procedures of OECD *Guidelines for Testing of Chemicals*, Test No. 404 "Acute Dermal Irritancy/Corrosion", 12 May 1991, and 405 "Acute Eye Irritancy/Corrosion" 24 Feb. 1987, respectively. When the results are assessed according to the criteria of European Commission Directive, 83/467/EEC, all of the compositions are classified as non-irritant to both dermal and ocular issue.

EXAMPLE 26

The compositions of Examples 1-12 are examined for toxicity to fish by the procedure of *OECD Guidelines for Testing of Chemicals*, Test No. 203, for April 1984 "Fish Acute Toxicity Test". When the results are assessed on the proposed toxicity rating scale for use at CNFRL (Columbia National Fisheries Research Laboratory, USA), the compositions are classified as "relatively non-toxic".

Although the invention has been described in terms of specified embodiments which are set forth in considerable detail, it is understood that this is by way of illustration only, and that alternative embodiments and operating techniques will become apparent to those skilled in the art in view of the disclosure. For example, one skilled in the art might substitute ethylene glycol for the propylene glycol disclosed herein, especially in a case where the quaternary ammonium compound contained a predominance of ethylene oxide units rather than propylene oxide units. Accordingly, modifications can be made without departing from the spirit of the described invention.

We claim:

1. A herbicidal composition which comprises: an aqueous solution of a herbicidally acceptable amount of a herbicidally acceptable salt of N-phosphonomethylglycine; a quaternary ammonium compound represented by the formula

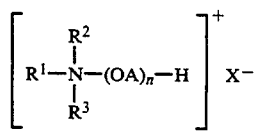

wherein each A represents an alkylene group having 2 or 3 carbon atoms, $R^1$ and $R^2$ are each independently an alkyl or alkanol group having from 1 to 3 carbon atoms; $R^3$ is an alkyl group having from 1 to 3 carbon atoms or a group having the formula $(AO)_m$—H; n (in a compound in which $R^3$ is an alkyl group) or n+m (in a compound in which $R^3$ is a group having the formula $(AO)_m$—H), has a value of from 2 to 15; and $X^-$ is a halide or phosphate; and polypropylene glycol having a molecular weight between about 300 and about 1000; wherein the weight ratio of N-phosphonomethylglycine to the quaternary ammonium compound is between about 1:5 to about 5:1, the weight ratio of polypropylene glycol to the quaternary ammonium compound is between about 1:40 and about 1:2 and the pH is between about pH 4.0 to about pH 7.0 to provide a clear composition.

2. A composition of claim 1 wherein the polypropylene glycol has a molecular weight above about 600.

3. A composition of claim 1 wherein the weight ratio of N-phosphonomethylglycine to quaternary ammonium compound is between about 1:2 to about 4:1.

4. A composition of claim 1 wherein $R^1$, $R^2$ and $R^3$ are each independently selected from methyl, ethyl and ethanol groups, and $X^-$ is chloride or phosphate.

5. A composition of claim 4 wherein —$(AO)_n$— is -ethylene oxide(propylene oxide)$_n$— wherein n is between 6 and 10.

6. A composition of claim 5 wherein the polypropylene glycol has an average molecular weight above about 600.

7. A composition of claim 1 wherein the herbicidally acceptable salt of N-phosphonomethylglycine is the isopropylamine salt, and the pH is between about pH 4.7 and about pH 6.0.

8. A composition of claim 1 wherein: the herbicidally acceptable salt of N-phosphonomethylglycine is the isopropylamine salt; $R^1$, $R^2$ and $R^3$ are each independently selected from methyl, ethyl and ethanol groups; $X^-$ is chloride or phosphate; —$(AO)_n$— is -ethylene oxide(propylene oxide)$_n$ where n is between 6 and 10.

9. A composition of claim 8 containing an additional amount of a water soluble salt to provide a clear solution at the natural pH of the solution.

10. A composition of claim 9 wherein the water-soluble salt is selected from the group consisting of tetramethyl ammonium chloride and tetraethyl ammonium chloride.

* * * * *